United States Patent [19]

Handjani et al.

[11] Patent Number: 4,608,211

[45] Date of Patent: Aug. 26, 1986

[54] PROCESS FOR PREPARING LIPID VESICLES BY VAPORISATION OF SOLVENTS

[75] Inventors: Rose-Marie Handjani; Alain Ribier, both of Paris; Manlio M. Maurelli, Vaujours, all of France

[73] Assignee: L'Oreal, Paris, France

[21] Appl. No.: 587,653

[22] Filed: Mar. 8, 1984

[30] Foreign Application Priority Data

Mar. 22, 1983 [FR] France ............................ 83 04674

[51] Int. Cl.⁴ .................... B01J 13/02; A61K 9/50; A61K 9/64
[52] U.S. Cl. ........................... 264/4.6; 222/94; 222/146.3; 222/635; 252/305; 424/38; 428/402.2; 436/829
[58] Field of Search ............... 264/4.6; 424/38; 436/829; 426/811

[56] References Cited

U.S. PATENT DOCUMENTS

| | | | |
|---|---|---|---|
| 2,524,590 | 10/1950 | Boe | 252/305 |
| 3,679,102 | 7/1972 | Charle et al. | 252/305 X |
| 4,188,412 | 2/1980 | Sejpal | 426/811 X |
| 4,247,411 | 1/1981 | Vanlerberghe et al. | 264/4.6 |
| 4,308,166 | 12/1981 | Marchetti et al. | 264/4.6 X |
| 4,394,372 | 7/1983 | Taylor | 424/85 |

FOREIGN PATENT DOCUMENTS 2325387 4/1977 France.

OTHER PUBLICATIONS

Puisieux et al. "Les Liposomes, Véhicules Possibles De Principes Actifs", Pharm. Acta. Helv., 52, Nr. 12 (1977), pp. 305-318.

Primary Examiner—Richard D. Lovering
Attorney, Agent, or Firm—Cushman, Darby & Cushman

[57] ABSTRACT

A process for preparing large unilamellar lipid vesicles is disclosed which process comprises preparing unilamellar lipid vesicles having an average diameter of at least 1,000 Å, each of these vesicles consisting of a spheroidal lipid lamella containing a substance to be encapsulated, which process comprises dissolving one or more lipids intended to form the lamella of the vesicles in at least one water-insoluble solvent, conditioning the resulting lipid solution at a pressure $P_1$ and at a temperature $\theta_1$, dissolving the substance to be encapsulated in water to obtain an aqueous phase, conditioning said aqueous phase at a pressure $P_2$ and a temperature $\theta_2$, injecting the lipid solution into the aqueous phase at a low flow rate so as initially to form droplets and so that solvent of the lipid solution vaporises on coming into contact with the said aqueous phase, the pressure $P_2$ being less than $P_1$ and less than the vapor pressure of the solvent in the said droplets at the temperature $\theta_2$.

15 Claims, 3 Drawing Figures

PROCESS FOR PREPARING LIPID VESICLES BY VAPORISATION OF SOLVENTS

The present invention relates to a process for preparing unilamellar lipid vesicles with an average diameter greater than 1,000 Å.

Lipid vesicles make it possible to encapsulate an aqueous liquid, for example an aqueous solution of a biologically active substance. It is known that, depending on the method which is employed to prepare these vesicles, one obtains either multilamellar vesicles (MLV), each of which consists of a plurality of spheroidal lipid lamellae, or unilamellar vesicles, each of which comprises only one lipid lamella. In this latter category, depending on the method of preparation employed, an average diameter less than 1,000 Å (SUV), or an average diameter greater than 1,000 Å (LUV) can be obtained.

Unilamellar vesicles obviously offer advantages over the multilamellar vesicles because the latter are heterogeneous in size and have a non-uniform number of lamellae. Further, among the unilamellar vesicles, those of the second category (LUV) have advantages over those of the first category (SUV) because, in view of their larger size, they offer a greater encapsulation capacity. Moreover, they make it possible to encapsulate macromolecular materials of a high molecular weight. As a result, on an industrial scale the aim is to obtain unilameller vesicles of the (LUV) type in the highest possible yield.

Two principal preparative methods are known at present for preparing this type of unilamellar vesicle: the method of detergent removal by dialysis and the solvent vaporisation method.

The paper by David S. Cafiso (Biochemica et Bio-Physica Acta, 649 (1981), 129-132, entitled "Preparation of unilamellar lipid vesicles at 37° C. by vaporization methods.") describes a process employing solvents with a low boiling point for preparing LUV type vesicles at physiological temperatures. According to this process, solutions containing solubilised lipids in ethyl methyl ether or dichlorofluoromethane at 4° C. are injected into a column of an aqueous buffer at 37° C. It is stated that the principal advantages of the process are, on the one hand, that heat-sensitive substances can be trapped more easily inside the vesicle without thermal denaturation and, on the other hand, that the number of lipids which are soluble in dichlorofluoromethane is greater than the number of lipids which can be dissolved in many other solvents. However, the fact remains that while this process, in which the injection step is carried out in a medium at 37° C., represents an improvement relative to previously known processes in which the injection medium is generally at a temperature of the order of 60° to 65° C., it nevertheless cannot be applied to substances which are sensitive to temperatures below 37° C.; at 37° C., for example, the denaturation of some proteins or the inactivation of some active molecules is observed.

Attempts have already been made to overcome these disadvantages. Thus in European Patent Application No. 0,055,576 an industrial process is proposed for manufacturing the vesicles under mild conditions (that is to say below the transition temperature of the lipid substances and without the need for a major disturbance of the receiving medium). According to this process, a system of solvents for the lipids is employed which comprises a water-soluble solvent S1 chosen from methanol, ethanol, propanol and isopropanol, and a hydrophobic solvent S2, more volatile than the aqueous solution, and which is chosen from hexane, cyclohexane, 2,2-dimethylbutane, pentane, isopentane and 1,1,2-trichlorotrifluoroethane. The fact that S2 has a boiling point (28° C.-81° C.) above the ambient temperature makes it necessary to raise the vesicle dispersion to a relatively high temperature to removed S2, and the fact that S1 is water-soluble makes it necessary to purify this dispersion by dialysis or filtration through a column in order to remove the solvent S1. As a result this process is not suitable for encapsulating heat-sensitive substances.

We had the idea that it would be possible to form vesicles at a low temperature if the pressure at which the aqueous phase which is to be encapsulated is conditioned is reduced. It was then observed that, if a lipid solution conditioned in a pressurised receptacle is injected at a reduced flow rate into an aqueous receiving medium under reduced pressure, then vesicles can be obtained in a very satisfactory yield at the abovementioned temperatures. The phenomenon observed is thought to be due to the combination of two factors: on the one hand, the injection is carried out at a reduced flow rate and, on the other hand, the pressure at which the aqueous phase which is to be encapsulated is conditioned is lower than the pressure at which the lipid solution is conditioned in the liquid state, and lower than the vapour pressure of the solvent(s) in the droplets formed at the point of injection at the temperature of the receiving medium.

In order to explain the greatly superior yield of the process according to the invention when compared to the known solvent vaporisation processes in which the lipid and receiving media are at normal pressure, the hypothesis has been put forward, although this invention is in no way bound by this, that, in the known processes, a relatively slow heat transfer takes place in the injection medium with lipid droplets dividing and thereby giving rise to relatively small vesicles (with an average diameter of 150 nm). In contrast, in the case of the present invention, it is observed that the droplets introduced into the receiving medium explode almost instantaneously, and this leads to unilamellar vesicles of a larger size. From this it follows that the "flash" in an aqueous medium which is produced according to the invention by reducing the pressure is not equivalent to the known flash due to a rise in temperature caused by injection into the receiving medium. The present invention makes it possible, moreover, to operate with any receiving temperature, which is preferably chosen to be less than 25° C. to permit the encapsulation of heat-sensitive substances.

Accordingly, the present invention provides a process for preparing unilamellar lipid vesicles having an average diameter above 1,000 Å, each of these vesicles consisting of a spheroidal lipid lamella inside which is placed a substance to be encapsulated, a process according to which the lipid(s) intended to form the lamella of the vesicles is, or are, dissolved in at least one water-insoluble solvent, the lipid solution is conditioned in the liquid state, conveniently in a receptacle, at a pressure $P_1$ and at a temperature $\theta_1$, the substance to be encapsulated is dissolved to obtain an aqueous phase, the said aqueous phase to be encapsulated is conditioned at a pressure $P_2$ and a temperature $\theta_2$, and the lipid solution is injected into the aqueous phase, so that the solvent(s)

of the lipid solution vaporise(s) on coming into contact with the said aqueous phase, characterised in that the lipid solution is injected into the aqueous phase to be encapsulated at a low flow rate to form droplets initially, the pressure $P_2$ being less than $P_1$ and less than the vapour pressure of the solvent(s) in the said droplets at the temperature $\theta_2$.

The temperatures $\theta_1$ and $\theta_2$ are preferably chosen to be substantially equal.

In a preferred embodiment of the process according to the invention, the lipid solution is conditioned in a receptacle of the "aerosol container" type which contains a propellent agent and the pressure $P_2$ is chosen below atmospheric pressure. It is then preferred, for reasons which are given later, to employ lipid(s) which is, or are, completely soluble in the liquid contents of the aerosol container. The pressure $P_1$ in the aerosol container is chosen to have a value, for example, from 1 to 8 bars absolute. Preferably, the pressure $P_1$ has a value from 4 to 6 bars absolute.

To permit heat-sensitive substances to be encapsulated, the solvent(s) chosen for the lipid is desirably a solvent which has a boiling point below 25° C. and the temperatures $\theta_1$ and $\theta_2$ are chosen to be substantially equal to ambient temperature. Furthermore, this solvent desirably has a low polarity. The solvents which meet the abovementioned conditions are particularly the halocarbons, among which can be mentioned trichlorofluoromethane, dichlorofluoromethane and dichlorodifluoromethane.

The propellent agent employed according to the invention may be a compressed gas which is soluble in the liquid phase contained in the aerosol container, nitrous oxide or carbon dioxide being capable of forming this gas. The propellent agent can also be a liquefied gas which is miscible with the lipid solution contained in the aerosol container, in particular a hydrocarbon which is or is not halogenated. Among such hydrocarbons there may be mentioned butane and propane and among the halocarbons, chlorofluoroalkanes such as dichlorofluoromethane, dichlorodifluoromethane, or 1,2-dichloro-1,1,2,2-tetrafluoroethane. The propellent agent can also consist of a compressed gas which is insoluble in the liquid phase contained in the aerosol container, for example nitrogen. When the propellent agent is a liquified gas which is miscible with the lipid solution in the aerosol container, it may reduce the solubility of the lipids in the solvent, in which case the propellant and the solvent in the aerosol container can be separated by a plastic or metal pouch.

According to the invention, the lipid(s) is, or are, dissolved in the chosen solvent generally at a concentration from 0.01 to 10 g per 100 ml of solvent.

Furthermore, in the case where use is made of ionic lipid(s), it is advantageous to employ an additional solvent which is more polar than the base solvent(s), to improve the solubility of this ionic lipid (or these ionic lipids). As an example of an additional solvent, mention can be made of ethyl methyl ether.

Furthermore, it is also possible to introduce into the lipid solution, lipophile substances to be encapsulated, these substances remaining in the walls of the vesicles which will subsequently be formed.

To produce the reduced flow rate of the lipid solution into the receptacle containing the aqueous phase to be encapsulated, use is made advantageously of a microvalve which can be controlled to provide a flow rate of, say, 5 ml per hour to 10 ml per minute.

Other preferred characteristics of the process according to the present invention are that: the pressure $P_2$ is from 0.1 mbar to 15 mbars; the lipid solution is conveyed to the receptacle containing the aqueous phase of the substance to be encapsulated by means of a capillary tube; the temperature $\theta_2$ of the phase to be encapsulated is kept constant and low by means of a thermostat; the temperature $\theta_2$ is below 25° C.; the aqueous phase to be encapsulated is gently agitated; in the case where the substance to be encapsulated is a non-degradable substance, the aqueous phase to be encapsulated is agitated mechanically, by means of ultrasonics; in the case where the substance to be encapsulated is a protein substance, an anti-foaming agent is introduced into the aqueous phase to be encapsulated.

Furthermore, according to the invention the vesicles can advantageously be produced continuously; in an advantageous embodiment, the lipid solution is injected into a channel in which the aqueous phase to be encapsulated is circulated.

In practice, when the process is carried out, the values of the flow rate produced by the microvalve and the value of the pressure $P_2$ are regulated as a function of the substance to be encapsulated. It can be stated that for solutes other than proteins, it is possible to employ a flow rate at the upper end of the range and to choose a pressure $P_2$ of 15 mbars and then of 0.1 mbar. On the other hand, for the encapsulation of protein products, during which there is a risk of formation of a stabilised foam, a low flow rate should be applied, together with a slightly reduced pressure.

It has been found that the heterogeneity of the vesicle distribution depends slightly on flow rate, moderately on the lipid concentration in the aerosol container and on the means of agitation of the aqueous solution, and considerably on the substance to be encapsulated and, in particular, on its viscosity, and on the flocculation of the vesicles formed in certain types of solute.

The final vesicle solution which is obtained by the process according to the invention generally has a lipid concentration from 0.1 to 10% by weight, and the encapsulated volume is usually greater than that obtained using the known methods of preparing vesicles.

The present invention also provides an apparatus intended for the use of the process defined above, characterised in that it comprises a first receptacle, of the aerosol container type, provided with a discharge valve and a second receptacle in which a reduced pressure can be established, means enabling the first and the second receptacles to be placed in communication for fluid, so that the contents of the first receptacle can be injected into the contents of the second receptacle, a microvalve being associated with the said means so that the injection flow rate can be controlled.

According to a preferred embodiment of the apparatus according to the invention, the means permitting the first and second receptacles to be placed in communication for fluid consist of a tubular transfer component connecting, at one of its ends, the outlet pipe of the discharge valve of the aerosol container and, at the other end, the inlet of the microvalve and a capillary distribution tube one end of which connects the outlet of the microvalve to the second receptacle. Preferably, the latter is a needle-microvalve.

Other preferred characteristics of the apparatus are as follows: the capillary tube has an internal diameter of approximately 0.3 mm; a diffuser device is fitted at the end of the distribution capillary tube; the second receptacle comprises a thermostat; the second receptacle comprises means enabling its contents to be agitated.

BRIEF DESCRIPTION OF DRAWINGS

The present invention will now be illustrated, merely by way of example, with reference to the accompanying drawings, in which.

Figure 1:
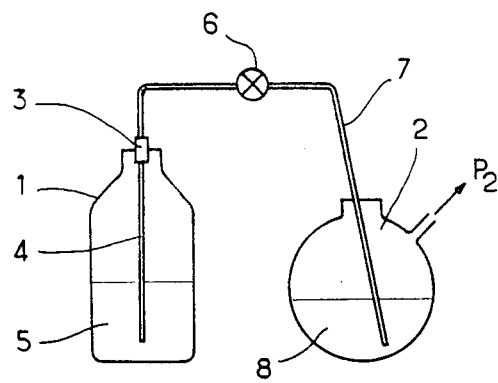
FIG. 1 shows diagrammatically an apparatus for using the process according to the invention.

The apparatus shown in FIG. 1 comprises a first receptacle, in the form of an aerosol container 1, and a second receptacle in the form of a flask, 2, in which a reduced pressure $P_2$ can be established.

The aerosol container 1 comprises a stop valve 3, as well as a tube 4 immersed in the liquid 5 which it contains. The outlet of the aerosol container is connected to a microvalve 6 at the outlet of which is arranged a capillary tube 7 immersed in liquid 8 in the flask 2. This capillary desirably has a diameter of approximately 0.3 mm and a length of 20 cm.

Figure 2:
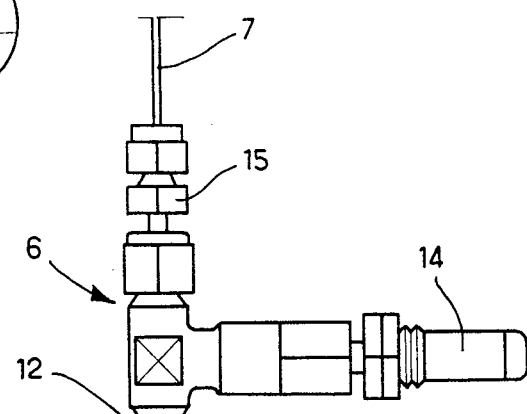
FIG. 2 shows, on a larger scale, a particular embodiment of the aerosol container which can be employed, on the outlet of which is fitted a microvalve intended to provide the reduced flow rate required by the process according to the invention.

In the particular embodiment of FIG. 2, a tubular transfer component 9 connects with the outlet pipe of the valve, 3 and with the inlet of the microvalve 6. For this purpose, the component 9 engages, through its outlet end, in central bore, 10, of a first ring 11, the bore 10 receiving at the other end outlet pipe 12 of the microvalve 6. Moreover, the ring 11, which acts as a clamping ring, is joined to a second ring 13 encircling the neck of the aerosol container 1. Both rings can be joined together by screwing together two concentric skirts 11a and 13a carried respectively by the rings 11 and 13.

The microvalve 6 is a needle-microvalve, which permits a very fine control by means of screw 14. It is possible, for example, to use "Nupro", reference SS2SG valve made of stainless steel. The capillary 7 is fitted to the outlet of the microvalve 6 by means of a coupling 15.

Figure 3:
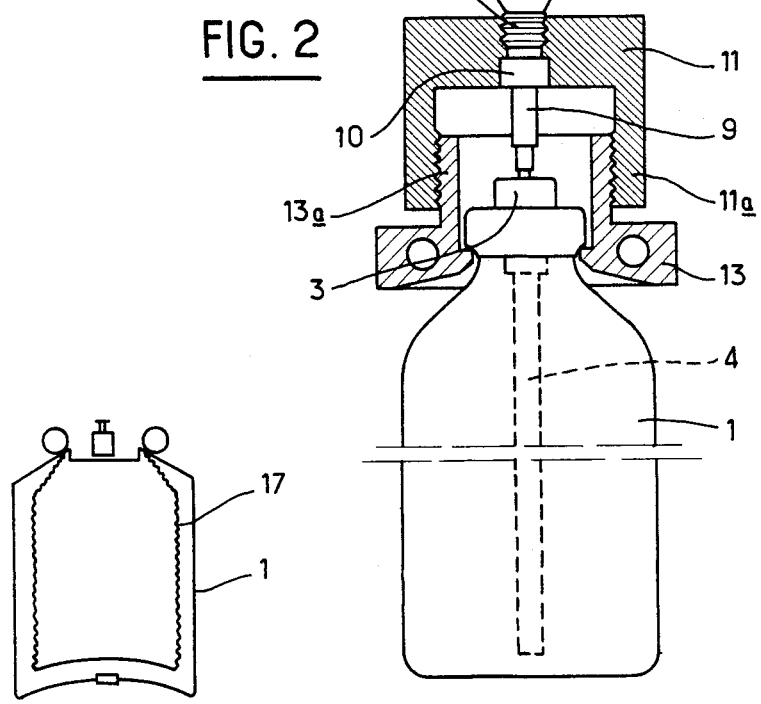
FIG. 3 shows diagrammatically a cross-section of an aerosol container intended to enclose a liquefied propellant capable of reducing the solubility of the lipids in the solvent.

In the particular case where the aerosol container 1 encloses a propellant consisting of a liquefied gas which is miscible with the lipid solution contained in the aerosol container and capable of reducing the solubility of the lipids in the solvents employed, the propellent agent is separated from the solvent in which the lipids are dissolved by a pouch of plastic or metal 17 (see FIG. 3), the propellant being arranged outside the pouch 17.

The following Example further illustrates the present invention, together with Comparative Examples A, B and C, according to which vesicles of an identical lipid composition are prepared by making use of known processes. Table I demonstrates that the volume encapsulated in the vesicles obtained by the Example of the present invention is much higher than that which can be encapsulated in vesicles obtained by the Comparative Examples.

The lipid composition employed for all these Examples (expressed in % by weight) is the following: -nonionic lipid compound of the general formula

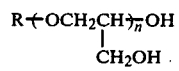

in which R is a hexadecyl radical and n has a statistical mean value of 3: 47.5%
cholesterol: 47.5%
dicetyl phosphate: 5%

EXAMPLE 1

Preparation of unilamellar lipid vesicles of the LUV type by the process according to the invention 0.5 g of the lipid mixture having the abovementioned composition is weighed into a 150-ml aerosol container. 100 g of trichlorofluoromethane are added. The aerosol container is clamped hermetically with a ring-valve-dip-pipe unit. The lipids are dissolved in their solvent by agitating the receptacle at a temperature of approximately 40° C.; then the material is allowed to cool to ambient temperature. 4 g of nitrous oxide are transferred to the aerosol container to establish a pressure of 6 bars therein. The aerosol container is then fitted with a device consisting of a transfer component, a needle-microvalve with micrometer control, a 0.3 mm bore capillary tube and a stainless metal mesh diffuser with two-micron meshes. The diffuser is immersed in 50 ml of 0.3 molar solution of glucose contained in an Erlenmeyer-type flat-bottomed container fitted with a vacuum connection. A magnetic bar stirrer is placed in the glucose solution. The Erlenmeyer is placed in a water bath thermostated at 20° C. and on a magnetic stirrer. The vacuum connection of the Erlenmeyer is connected to a water pump providing a reduced pressure of 15 mbars. The microvalve is adjusted to give a flow rate of 3 ml per minute. The aqueous dispersion of the vesicles which are thus formed is subjected to a reduced pressure of 0.1 mbar for an hour in order to extract the last traces of solvent. The vesicle dispersion is obtained at a lipid concentration of 1%. The mean size is determined as 300 nm by means of a quasi-elastic diffusion granulometer (Nanosizer). The swelling ratio is determined as 18 μl/mg of lipids by assay of the encapsulated glucose.

COMPARATIVE EXAMPLE A

Preparation of multilamellar vesicles by ultra-dispersion

This process is that described in French Pat. No. 2,315,991.

8 g of the lipid mixture of the abovementioned composition are weighed into a 250-ml stainless steel beaker and are melted at 100°–120° C. At 80° C., 20 g of a 0.3 molar aqueous solution of glucose are added and the lipid phase thus formed (lamellar phase) is homogenised with the aid of a metal spatula. 72 g of the 0.3M aqueous solution of glucose are then added. The mixture is subjected to the action of a Virtis model 60 K ultradisperser. The turbine speed is set at 40,000 revolutions per minute and the agitation is continued for 30 minutes. Heating of the vesicle dispersion is limited by immersing it in a water bath thermostated at 20° C. The vesicle dispersion is obtained at a lipid concentration of 8%. The mean size is determined as ≧300 nm by examination using the Nanosizer. The swelling ratio is determined as 7 μl/mg of lipids by assaying the encapsulated glucose.

COMPARATIVE EXAMPLE B

Preparation of unilamellar vesicles of the SUV type using the ultrasound process 0.3 g of the lipid mixture with the abovementioned composition is weighed into a 100-ml round flask. The mixture is dissolved in 5 ml of a mixture of chloroform and methanol in the ratio 2:1. The solvent is evaporated off by means of a rotary evaporator; then the last traces of solvent are removed by placing the product mixture for an hour under reduced pressure generated by a vane pump. The lipid film obtained is placed in contact with 10 ml of a 0.3 molar aqueous solution of glucose. The flask, placed on a shaker, is vigorously agitated for two hours at a temperature of 60° C., and then while cooling gradually to return to ambient temperature. The vesicle dispersion is then subjected to the action of ultrasound by 20 minutes' contact with a microprobe connected to a Branson generator of the Sonifier B 30 type. During the ultrasonic treatment, heating of the vesicle dispersion is limited by the use of a water bath thermostated at 20° C. The vesicle dispersion is obtained at a lipid concentration of 3%. The mean size is determined as 90 nm by examination using the Nanosizer. The swelling ratio is determined as 2 µl/mg of lipids by assay of the encapsulated glucose.

COMPARATIVE EXAMPLE C

Preparation of unilamellar lipid vesicles of the LUV type by dialysis 0.15 g of the lipid mixture with the abovementioned composition is weighed into a 100-ml round flask. The lipids are dissolved in 3 ml of a mixture of chloroform and methanol in the ratio 2:1. The solvent is evaporated off by means of a rotary evaporator, then the last traces of solvent are removed by subjecting the product mixture for an hour to the reduced pressure generated by a vane pump. The lipid film obtained is placed in contact with 10 ml of a 0.3 molar aqueous solution of glucose. The flask, placed on a shaker, is vigorously agitated for two hours at a temperature of 60° C. 600 mg of octylglucoside are then added while the shaking is continued for two hours at 60° C. The micellar solution thus obtained is clear. 5 ml of this solution are introduced into the dialysis cell of the LIPOPREP DIACHEMA "Bilayer Liposome Preparation Device". The controls are set to obtain the following conditions:

dialysis compartment temperature: 60° C. for eighteen hours, then progressive cooling from 60° to 25° C. over four hours;

dialysis flow rate: 2 ml per minute for each of the two half-cells;

dialysis solution: 0.3 molar glucose stirring rate of the magnetic bar in the cell: 100 revolutions/minute.

The vesicle dispersion is obtained at a lipid concentration of 1.5%. The size is determined as 150 nm by examination using the Nanosizer. The swelling ratio is determined as 4 µl/mg of lipids by assay of the encapsulated glucose.

TABLE I

| Vesicle type | Method | Mean size (nm) | Encapsulated volume* (µl/mg lipids) | Incompatibility with |
|---|---|---|---|---|
| MLV | Ultra-dispersion Example A | 300 | 7 | Substances sensitive to temperature and mechanical stirring. |
| SUV | Ultrasound Example B | 90 | 2 | Substances sensitive to temperature and mechanical stirring. |
| LUV | Dialysis Example C | 150 | 4 | Heat-sensitive substances |
| LUV | Process according to the invention Example 1 | 300 | 18 | none |

*determined by enzyme microassay of an encapsulated solute glucose.

The vesicles formed in a 0.3M solution of glucose are filtered through a column of gel—Pharmacia Sephadex G 50 coarse type—eluted with a 0.15 molar aqueous solution of sodium chloride. The vesicles thus washed free of all traces of unencapsulated glucose are then micellised by a surface-active agent such a Triton X 100 (octylphenoxypolyethoxyethanol), which permits the glucose encapsulated earlier to be released and subsequently assayed.

We claim:

1. Process for preparing unilamellar lipid vesicles having an average diameter of at least 1,000 Å, each of these vesicles consisting of a spheroidal lipid lamella containing a substance to be encapsulated, which process comprises dissolving one or more lipids intended to form the lamella of the vesicles in at least one water-insoluble solvent, conditioning the resulting lipid solution at a pressure $P_1$ and at a temperature $\theta_1$, dissolving the substance to be encapsulated in water to obtain an aqueous phase, conditioning said aqueous phase at a pressure $P_2$ and a temperature $\theta_2$, injecting the lipid solution into the aqueous phase at a low flow rate so as initially to form droplets and so that solvent of the lipid solution vaporises on coming into contact with the said aqueous phase, the pressure $P_2$ being less than $P_1$ and less than the vapour pressure of the solvent in the said droplets at the temperature $\theta_2$.

2. Process according to claim 1, in which the temperatures $\theta_1$ and $\theta_2$ are substantially equal.

3. Process according to claim 2 in which the lipid solution contains from 0.01 to 10 g per 100 ml of solvent.

4. Process according to claim 1 in which the lipid solution is conditioned in a receptacle of the "aerosol container" type which contains a propellant agent and the pressure $P_2$ is below atmospheric pressure.

5. Process according to claim 4 in which the pressure $P_1$ is from 1 to 8 bars absolute.

6. Process according to claim 4 in which a compressed gas which is soluble in the liquid phase contained in the aerosol container is the propellant agent.

7. Process according to claim 4 in which a liquefied gas which is miscible with the lipid solution contained in the aerosol container is the propellant agent.

8. Process according to claim 7 in which a hydrocarbon which is or is not halogenated is the propellant agent.

9. Process according to claim 4 in which a compressed gas which is insoluble in the liquid phase contained in the aerosol container is the propellant agent.

10. Process according to claim 1 in which the solvent for the lipid has a boiling point below 25° C., and the temperature $\theta_1$ and $\theta_2$ are substantially equal to ambient temperature.

11. Process according to claim 10 in which the said solvent is a halocarbon.

12. Process according to claim 1 in which a microvalve is employed to provide the reduced flow rate of the lipid solution into the aqueous phase to be encapsulated and the microvalve is regulated to provide a flow rate of 5 ml per hour to 10 ml per minute.

13. Process according to claim 1 in which the pressure $P_2$ is from 0.1 mbar to 15 mbars.

14. Process according to claim 1 in which the vesicles are produced continuously.

15. Process according to claim 14 in which the lipid solution is injected into a channel in which the aqueous phase to be encapsulated is circulated.

* * * * *